United States Patent [19]
Ataka et al.

[11] Patent Number: 6,100,239
[45] Date of Patent: Aug. 8, 2000

[54] 13-MEMBERED RING MACROLIDE COMPOUND, MEDICINE CONTAINING THE SAME, AND PROCESS FOR PRODUCING THE SAME

[75] Inventors: Kikuo Ataka; Hiroyuki Miyata; Akira Takama, all of Ube, Japan

[73] Assignee: Chugai Seiyaku Kabushiki Kaisha, Japan

[21] Appl. No.: 09/308,879

[22] PCT Filed: Nov. 25, 1997

[86] PCT No.: PCT/JP97/04277

§ 371 Date: May 25, 1999

§ 102(e) Date: May 25, 1999

[87] PCT Pub. No.: WO98/23629

PCT Pub. Date: Jun. 4, 1998

[30] Foreign Application Priority Data

Nov. 26, 1996 [JP] Japan ................................. 8-314526

[51] Int. Cl.[7] ............................ A61K 31/70; C07H 17/08
[52] U.S. Cl. ................................ 514/29; 536/7.2; 536/7.4
[58] Field of Search ........................ 536/7.2, 7.4; 514/29

[56] References Cited

U.S. PATENT DOCUMENTS

| | | | |
|---|---|---|---|
| 3,674,773 | 7/1972 | Kurath | 536/7.2 |
| 3,816,397 | 6/1974 | Soloman et al. | 536/7.2 |
| 5,658,888 | 8/1997 | Koda et al. | 514/29 |
| 5,712,253 | 1/1998 | Lartey et al. | 514/28 |
| 5,912,235 | 6/1999 | Hoeltje et al. | 514/28 |

OTHER PUBLICATIONS

C. Burnell–Curty et al, "A Novel . . . Contraction", J. Org. Chem., vol. 61, No. 15, (1996) pp. 5153–5154.

*Primary Examiner*—Deborah C. Lambkin
*Attorney, Agent, or Firm*—Bierman, Muserlian and Lucas

[57] ABSTRACT

The present invention discloses the compound represented by the formula (I)

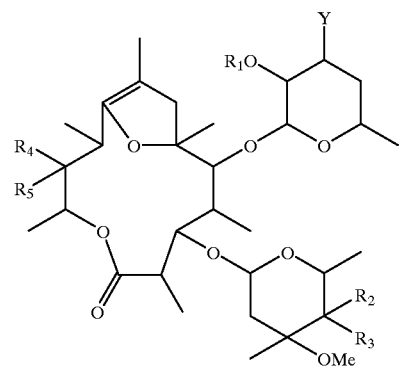

(I)

wherein $R_1$ and $R_2$ are hydrogen atoms, $R_3$ represents a hydrogen atom, a hydroxyl group or an amino group, or $R_2$ and $R_3$ in combination represent =O or =NOR$_{11}$, where $R_{11}$ represents a hydrogen atom or a lower alkyl group, $R_4$ and $R_5$ in combination represent =O, Y represents —N($R_6$) ($R_7$) or —N$^+$($R_8$) ($R_9$) ($R_{10}$)X$^-$; where $R_6$ to $R_{10}$ each represent a hydrogen atom, a lower alkyl group, etc., and X$^-$ represents an anion, a pharmaceutical composition containing the same and a process for producing the same.

6 Claims, No Drawings

13-MEMBERED RING MACROLIDE COMPOUND, MEDICINE CONTAINING THE SAME, AND PROCESS FOR PRODUCING THE SAME

This application is a 371 of PCT/JP97/04277 Nov. 25, 1997.

TECHNICAL FIELD

This invention relates to a 13-membered ring macrolide compound or a salt thereof which acts to stimulate the contractile motility of alimentary canals of mammals and is thus useful as a stimulant for the contractile motility of alimentary canals.

BACKGROUND ART

On the basis of differences in their mechanisms, prokinetic agents are roughly classified into 4 groups: direct cholinergic drugs (aclatonium napadisilate); indirect cholinergic drugs (cisapride); dopamine blockers (domperidone); and opiate agonists (trimebutine maleate), and are widely used as therapeutic agents for dysfunction of enterokinesis, particularly for symptoms of digestive organs such as gastrointestinal complaints due to hypokinesia. However, these drugs have adverse effects such as extra-pyramidal symptoms or stimulation of prolactin release caused by the dopamine blocking action. In addition, it is known that the action of these drugs, which is different from that of a spontaneous, physiological movement propagating from the upper gastrointestinal tract to the lower gastrointestinal tract, often leads to the onset of adverse effects such as diarrhea, emesis or the like.

On the other hand, motilin is known as a gastrointestinal hormone which stimulates the contractile motility of alimentary canals, but its supply by extraction from natural sources or by chemical synthesis has not been satisfactory, and thus a large supply thereof has been difficult to secure. Further, motilin is a peptide consisting of 22 amino acids, so the development of an oral preparation comprising it has been difficult.

In recent years, erythromycin and its derivatives have been found to have a powerful stimulating activity with respect to the contractile motility of alimentary canals, of which activity is similar to that of motilin (see Japanese Patent Application Disclosures SHO No. 60-218321, SHO No. 61-87625, SHO No. 63-99016, SHO No. 63-99092, HEI No. 6-56873, and The Journal of Pharmacology and Experimental Therapeutics, vol. 251, No. 2, pp. 707–712, 1989). However, each of these compounds is a 14-membered ring macrolide compound, and a 13-membered ring macrolide compound has never been known.

The present inventors have intensively studied to provide a substance which is capable of stimulating the contractile motility of alimentary canals and of being supplied with a large amount. As a result, they have succeeded in synthesizing a novel 13-membered ring macrolide compound using antibiotic erythromycin A as a starting material. They have investigated the pharmacological activity of the compound, and have found that the novel 13-membered ring macrolide has a powerful stimulating activity with respect to the contractile motility of alimentary canals.

Accordingly, an object of the present invention is to provide a novel 13-membered ring macrolide which is capable of stimulating the contractile motility of alimentary canals and of being supplied with a large amount.

DISCLOSURE OF THE INVENTION

The present invention relates to a compound represented by the formula (I):

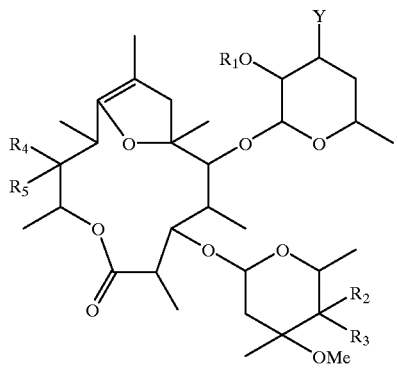

(I)

wherein $R_1$ represents a hydrogen atom or an acyl group; $R_2$ and $R3$ may be the same or different, and each represents a hydrogen atom, a hydroxyl group, an acyloxy group or an amino group, or $R_2$ and $R_3$ in combination represent $=O$ or $=NOR_1$; where $R_{11}$ represents a hydrogen atom or a lower alkyl group; $R_4$ and $R_5$ may be the same or different, and each represents a hydrogen atom or a hydroxyl group, or $R_4$ and $R_5$ in combination represent $=O$ or $=NOR_{11}$; Y represents $—N(R_6)$ $(R_7)$ or $—N^+(R_8)$ $(R_9)$ $(R_{10})X^-$; where $R_6$, $R_7$, $R_8$, $R_9$ and $R_{10}$ may be the same or different, and each represents a hydrogen atom, an acyl group, an unsubstituted or substituted lower alkyl group, an unsubstituted or substituted lower alkenyl group, an unsubstituted or substituted lower alkynyl group, an unsubstituted or substituted cycloalkyl group, or a monocyclic, saturated, 3- to 7-membered heterocyclic ring comprising an oxygen atom, a sulfur atom or a nitrogen atom as a hetero atom which may have a substituent(s), or $R_6$ and $R_7$, or $R_8$ and $R_9$ may form an azacycloalkyl group together with the neighboring nitrogen atom, respectively; and $X^-$ represents an anion, or a salt thereof.

BEST MODE FOR CARRYING OUT THE INVENTION

In the present invention, as the acyl group represented by $R_1$ in the 13-membered ring macrolide compound (hereinafter referred to as Compound (I)) represented by the formula (I), there may be mentioned, for example, a formyl group, an acetyl group, a propionyl group, a butyryl group, a pivaloyl group, a benzoyl group, an ethoxycarbonyl group, a tert-butoxy-carbonyl group, a benzyloxycarbonyl group, etc., and preferably a benzyloxycarbonyl group or an acetyl group.

As the acyloxy group represented by $R_2$ and $R_3$, there may be mentioned a formyloxy group, an acetyloxy group, a propionyloxy group, a butyryloxy group, a pivaloyloxy group, a benzoyloxy group, an ethoxycarbonyloxy group, a t-butoxycarbonyloxy group, a benzyloxycarbonyloxy group, etc.

The lower alkyl group of $R_{11}$ in $=NOR_{11}$ formed by $R_2$ and $R_3$ or $R_4$ and $R_5$ in combination means an alkyl group having 1 to 6 carbon atoms.

As the acyl group represented by $R_6$, $R_7$, $R_8$, $R_9$ and $R_{10}$, there may be mentioned a formyl group, an acetyl group, a propionyl group, a butyryl group, a pivaloyl group, a benzoyl group, an ethoxycarbonyl group, a tert-butoxycarbonyl group or a benzyloxycarbonyl group, etc., and preferably a benzyloxycarbonyl group.

As the lower alkyl group, there may be mentioned an alkyl group having 1 to 6 carbon atoms, preferably a methyl group, an ethyl group, a n-propyl group, an i-propyl group, a n-butyl group, a sec-butyl group or a tert-butyl group.

As the lower alkenyl group, there may be mentioned an alkenyl group having 2 to 6 carbon atoms, preferably a vinyl group, an allyl group, a 1-butenyl group, a 2-butenyl group or a 3-butenyl group.

As the lower alkynyl group, there may be mentioned an alkynyl group having 2 to 6 carbon atoms, preferably an ethynyl group, a propargyl group or a butynyl group.

As the cycloalkyl group, there may be mentioned a cycloalkyl group having 3 to 8 carbon atoms, preferably a cyclopropyl group, a cyclobutyl group, a cyclopentyl group or a cyclohexyl group.

As the monocyclic, saturated, 3- to 7-membered heterocyclic ring comprising an oxygen atom, a sulfur atom or a nitrogen atom as a hetero atom, there may be mentioned a tetrahydrofuranyl group, an oxetanyl group, a tetrahydrothienyl group, an azethidyl group, a pyrrolidinyl group or a piperidyl group.

The azacycloalkyl group formed by $R_6$ and $R_7$ or $R_8$ and $R_9$ together with the neighboring nitrogen atom means a group in which one or more carbon atoms of the cycloalkyl group is/are replaced with a nitrogen atom(s), and there may be mentioned, for example, an aziridinyl group, an azetidinyl group, a pyrrolidinyl group, a piperidino group, a hexamethyleneimino group, etc.

In the present invention, in Compound (I), the expressions "unsubstituted or substituted", and "which may have a substituent(s)" regarding $R_6$, $R_7$, $R_8$, $R_9$ and $R_{10}$ mean that the lower alkyl group, the lower alkenyl group, the lower alkynyl group, the cycloalkyl group, or the monocyclic, saturated, 3- to 7-membered heterocyclic ring comprising an oxygen atom, a sulfur atom or a nitrogen atom as a hetero atom 1) has no substituent, or
2) has a substituent(s).

As the above substituent (s), there may be mentioned, for example, a hydroxyl group(s), an amino group(s), a halogen atom(s), a cyano group(s), an alkyloxy group(s), a mercapto group(s), an acyl group(s), a carbamoyl group(s), etc.

In Compound (I), when Y represents $-N^+(R_8)(R_9)(R_{10})X^-$, as the anion represented by $X^-$, there may be mentioned, for example, a chlorine ion, a bromine ion, an iodine ion, a trifluoroacetic acid ion, or a trifluoromethanesulfonic acid ion, etc.

In Compound (I), the compound wherein $R_1$ and $R_2$ are hydrogen atoms, $R_3$ is a hydrogen atom, a hydroxyl group or an amino group, or $R_2$ and $R_3$ represent $=O$ or $=N-OR_{11}$ in combination, $R_{11}$ is a hydrogen atom or a lower alkyl group, $R_4$ and $R_5$ represent $=O$ in combination, Y is $-N(R_6)(R_7)$ or $-N^+(R_8)(R_9)(R_{10})X^-$, $R_6$, $R_7$, $R_8$, $R_9$ and $R_{10}$ may be the same or different, and each represents a hydrogen atom, an unsubstituted or substituted lower alkyl group, an unsubstituted or substituted lower alkynyl group, an unsubstituted or substituted lower alkenyl group, an unsubstituted or substituted cycloalkyl group, or a monocyclic, saturated, 3- to 7-membered heterocyclic ring comprising an oxygen atom, a sulfur atom or a nitrogen atom as a hetero atom which may have a substituent(s), and the substituent(s) is a hydroxyl group(s), an amino group(s), a halogen atom(s), a cyano group(s), an alkyloxy group(s), a mercapto group(s), an acyl group(s) or a carbamoyl group(s), and $X^-$ is an anion, or a salt thereof shows an affinity to a motilin receptor, and, as shown in Test examples mentioned hereinbelow, it has an excellent enterokinesis stimulating activity, and is thus useful as a stimulant for the contractile motility of alimentary canals of mammals.

The compound of the formula (I) according to the present invention can be obtained by allowing the compound represented by the formula (II):

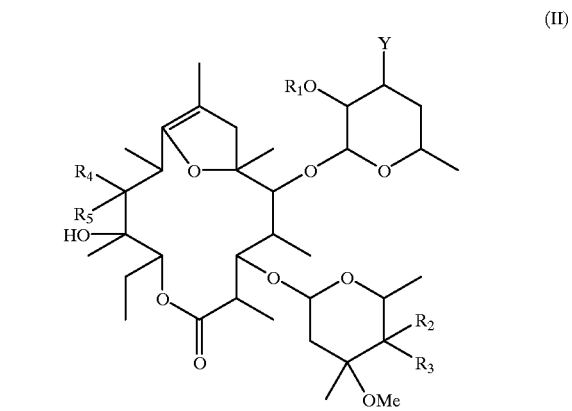

(II)

wherein $R_1$, $R_2$, $R_3$, $R_4$, $R_5$ and Y have the same meanings as defined above, to react with a base such as an alkali metal alcoholate, an alkali metal hydroxide, an alkaline earth metal hydroxide, an alkali metal carbonate, sodium hydride, sodium amide, an alkyl lithium, an alkyl amine, and the like in a solvent, for example, in water, an organic solvent(s) or a mixture of water and an organic solvent(s), at $-20$ to $70°$ C. to effect an intramolecular transformation reaction of the ring (see Step 2 mentioned hereinbelow). The compound of the formula (II) has already been known in Japanese Patent Application Disclosures Hei No. 6-56873, HEI No. 6-211886, and HEI No. 8-245684.

Also, after the above-mentioned transformation reaction of the ring, the substituent $-N(Me)2$, $-NHMe$ or $-NH_2$ represented by Y of the formula (I) is converted into the other Y according to the method described in the examples of the above publications, so that a different compound of the formula (I) can be produced.

Compound (I) can be obtained, for example, by steps (1) to (7) represented in the following reaction scheme (1-1):

Reaction Scheme (1 - 1)
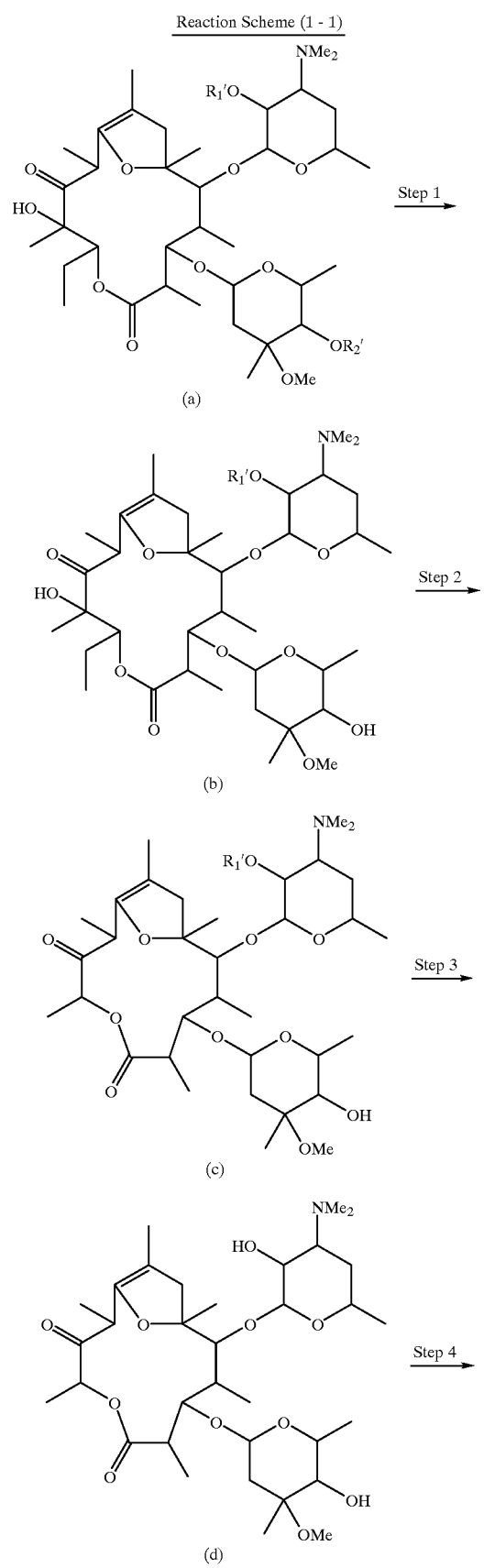
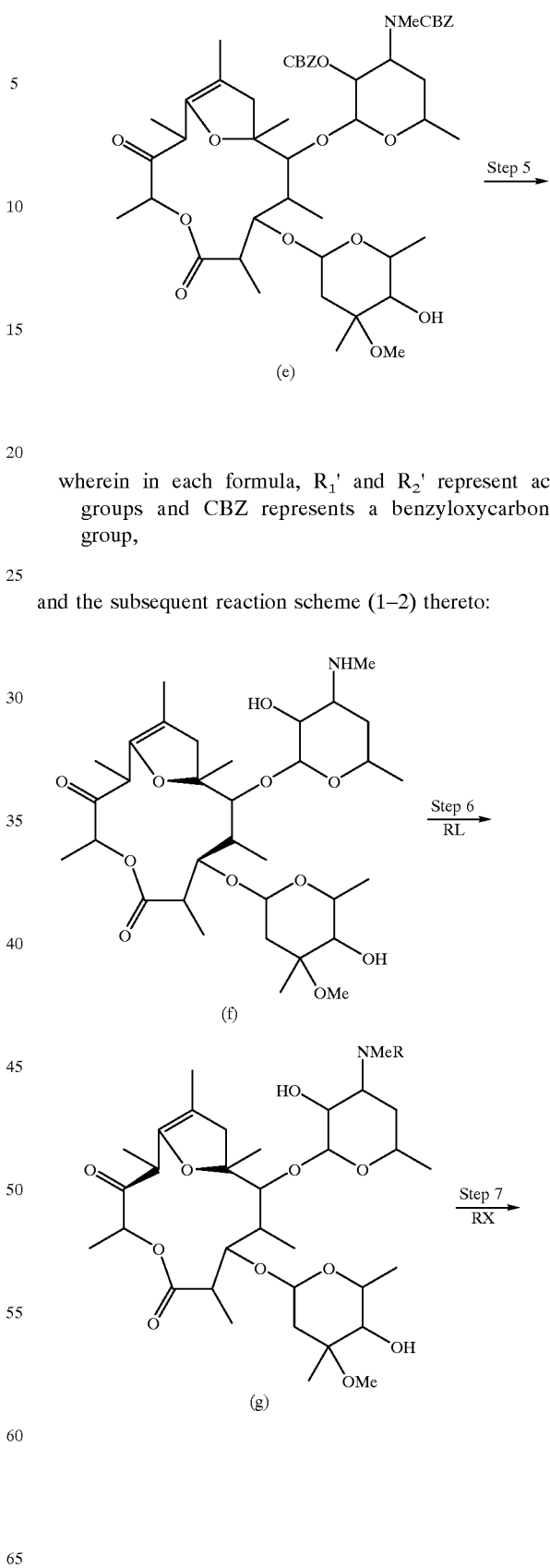
wherein in each formula, $R_1'$ and $R_2'$ represent acyl groups and CBZ represents a benzyloxycarbonyl group,
and the subsequent reaction scheme (1–2) thereto:

-continued

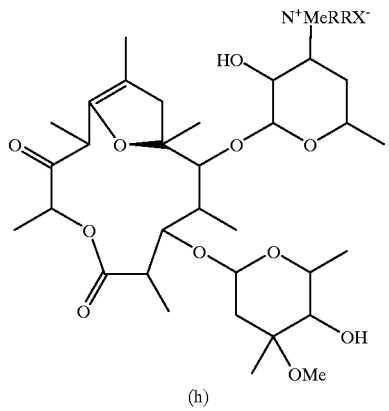

(h)

wherein R represents an unsubstituted or substituted lower alkyl group, an unsubstituted or substituted lower alkenyl group, an unsubstituted or substituted lower alkynyl group, an unsubstituted or substituted cycloalkyl group, or a monocyclic, saturated, 3- to 7-membered heterocyclic ring comprising an oxygen atom, a sulfur atom or a nitrogen atom as a hetero atom which may have a substituent(s), L is a halogen atom, an OTs (para-toluenesulfonyloxy) group or an OMs (methanesulfonyloxy) group, and X represents chlorine, bromine or iodine, a trifluoroacetyloxy group or a trifluoromethanesulfonyloxy group, etc.

In the following, the respective steps are explained.

Step (1); 2'-O-acyl-4"-O-acyl-11-oxo-8,9-anhydro-erythromycin A (described in Japanese Patent Application Disclosure HEI No. 6-56873) shown by the formula (a) (wherein $R_1'$ and $R_2'$ represent acyl groups) is dissolved in an inert solvent and is subjected to deacylation reaction in the presence of a base to produce the compound represented by the formula (b).

Here, as the inert solvent, there may be mentioned, for example, acetone, ether, tetrahydrofuran, dioxane, di-chloromethane, chloroform, N,N-dimethylformamide, acetonitrile, dimethylsulfoxide, etc., or a mixed solvent thereof, preferably tetrahydrofuran.

As the base, there may be mentioned, for example, sodium hydride, sodium hydroxide, potassium hydroxide, etc.

The reaction temperature is generally −20 to 50° C., preferably 0 to 30° C.

Step (2); The compound of the formula (b) (wherein $R_1'$ represents an acyl group) obtained in step (1) is subjected to intramolecular transformation reaction of the ring in the presence of a base, in a solvent, whereby the compound of the present invention represented by the formula (c) (wherein $R_1'$ represents an acyl group) can be produced.

The solvent is not particularly limited, and, there may be mentioned, for example, water, an organic solvent(s) or water+an organic solvent(s), preferably a mixed solvent of water+an organic solvent(s).

As the organic solvent, there may be mentioned, for example, an aromatic hydrocarbon series organic solvent such as benzene, toluene, xylene, etc.; an ether series organic solvent such as ethyl ether, butyl ether, tetrahydrofuran, dioxane, etc.; an aliphatic alcohol series organic solvent such as methanol, ethanol, propanol, butanol, etc.; a halogenated hydrocarbon series organic solvent such as methylene chloride, 1,2-dichloroethane, etc.; a nitrile series organic solvent such as acetonitrile, etc.; an aprotic polar organic solvent such as N,N-dimethylformamide, dimethylsulfoxide, etc., preferably an ether series organic solvent.

As the base, there may be mentioned, for example, an alkali metal alcoholate such as sodium methylate, sodium ethylate, sodium propylate, sodium butylate, potassium methylate, potassiumethylate, potassiumpropylate, potassium butylate, etc.; an alkali metal hydroxide such as sodium hydroxide, potassium hydroxide, etc.; an alkaline earth metal hydroxide such as magnesium hydroxide, calcium hydroxide, etc.; an alkali metal carbonate such as sodium carbonate, potassiumcarbonate, etc.; sodiumhydride; sodiumamide; alkyl lithium; and an amine such as triethylamine, trimethylamine, tributylamine, etc., preferably an alkali metal hydroxide or sodium hydride, more preferably sodium hydroxide, potassium hydroxide or sodium hydride.

The reaction temperature is generally −20 to 70° C., preferably 0 to 40° C.

Step (3); The compound represented by the formula (c) obtained in Step (2) is dissolved in a lower alcohol in the presence or absence of a base, whereby an acyl-protecting group ($R_1'$) at the 2'-position is removed to produce the compound of the present invention represented by the formula (d).

As the lower alcohol, there may be mentioned, for example, an aliphatic lower alcohol such as methanol, ethanol, propanol or butanol, etc., preferably methanol.

As the base, the same base as used in Step (2) can be used.

The reaction temperature is generally '20 to 80° C., preferably 20 to 60° C.

Step (4); The compound represented by the formula (d) obtained in Step (3) is reacted with benzyloxycarbonyl chloride in an inert solvent in the presence of a base, whereby the compound of the present invention represented by the formula (e) (wherein CBZ has the same meaning as defined above) can be produced.

As the inert solvent, there may be mentioned an aromatic hydrocarbon series organic solvent such as benzene, toluene, xylene, etc.; an ether series organic solvent such as ethyl ether, butyl ether, tetrahydrofuran, dioxane, etc.; a halogenated hydrocarbon series organic solvent such as methylene chloride, 1,2-dichloroethane, etc.; a nitrile series organic solvent such as acetonitrile, etc.; acetone, etc., preferably an aromatic hydrocarbon series organic solvent, particularly preferably toluene.

As the base, there may be mentioned, for example, an alkali metal carbonate such as sodium carbonate, potassium carbonate, etc.; an alkali metal hydrogen carbonate such as sodium hydrogen carbonate, potassium hydrogen carbonate, etc.; an amine such as triethylamine, trimethylamine, tributylamine, etc., preferably sodium hydrogen carbonate or potassium hydrogen carbonate.

The reaction temperature is generally 0 to 80° C., preferably room temperature to 50° C.

Step (5); The benzyloxycarbonyl groups at the 2'-position and the 3'-position of the compound represented by the formula (e) obtained in Step (4) are removed by using a hydrogen gas (3 to 4 atm) or a compound available as a hydrogen source in the presence of a metal catalyst such as palladium, etc., to produce the compound of the present invention represented by the formula (f).

Here, as the compound available as a hydrogen source, there may be mentioned, for example, formic acid, ammonium formate, sodium formate, etc., preferably ammonium formate.

Step (6); The compound represented by the formula (III):

RL wherein R and L have the same meanings as defined above, is reacted with the compound represented by the formula (f) obtained in Step (5) in an inert solvent in the presence of a base to produce the compound represented by the formula (g). (see Japanese Patent Application Disclosures HEI No. 6-56873, HEI No. 6-211886, SHO No. 63-99092)

The expressions "unsubstituted or substituted" and "which may have a substituent (s)" represented by R in Compound (III) have the same meaning as the "unsubstituted or substituted" and "which may have a substituent (s)" regarding he above-mentioned $R_6$, $R_7$, $R_8$, $R_9$ and $R_{10}$.

The halogen atom represented by L is a fluorine atom, chlorine atom, a bromine atom or an iodine atom.

As the inert solvent, there may be mentioned, for example, dimethylsulfoxide, N,N-dimethylformamide, dimethoxyethane, tetrahydrofuran, dioxane, 1,2-dimethoxyethane, acetone, acetonitrile, 1,3-dimethylimidazolidone or a mixed solvent hereof.

As the base, the same base used in Step (4) can be used.

The reaction temperature is generally 0 to 150° C., preferably 60 to 110° C.

Step (7); The compound represented by the formula (g) obtained in Step (6) is further reacted with the compound represented by the formula (IV):

RX wherein R and X have the same meanings as defined above, to obtain the compound (h) wherein Y is $-N^+(R_8)(R_9)(R_{10})X^-$ (wherein $R_8$, $R_9$ and $R_{10}$ have the same meanings as in the above-mentioned R, and $X^-$ has the same meaning as defined above).

Besides, among the compounds represented by the formula (I), a compound in which $R_4$ and $R_5$ form $=O$ in combination is reacted with a suitable reducing agent whereby a compound wherein $R_4$ or $R_5$ is a hydroxyl group can be obtained.

Also, the compound (I) or a salt thereof according to the present invention can be obtained by applying the specific preparation methods described in Examples.

The above-mentioned compound or a salt thereof can be formulated with usual pharmaceutical excipients, for example, water, organic or inorganic inert carrier substances such as gelatin, lactose, starch, magnesium stearate, talc, vegetable oil, gum, polyalkylene glycol, etc., to produce a usual pharmaceutical preparation, which is effective by oral or parenteral administration. The pharmaceutical preparation can be used in the form of solids, for example, tablets, a suppositories, capsules, or in the form of liquids, for example, liquids and solutions, suspensions or emulsions. Other pharmaceutical additives may be added thereto, and include, for example, preservatives, stabilizers, wetting agents or emulsifiers, salts which change osmotic pressure or act as buffers. The pharmaceutical preparation may also contain other substances which are active for treatment.

Daily administration doses of the above-mentioned compounds may vary depending on the respective compounds to be used, administration routes and the conditions of the patient, but the oral preparations are preferably administered with daily doses in the range from 0.1 mg to 200 mg to an adult.

The parenteral preparations are preferably administered with daily doses in the range from 0.01 mg to 20 mg to an adult.

In the following, production of the compounds of the present invention is explained in greater detail with reference to Examples, but it should be understood that the present invention is by no means limited to these examples.

EXAMPLES

Example 1

(1) In 25 ml of tetrahydrofuran (THF) was dissolved 5.0 g of 2'-O-acetyl-4"-O-formyl-11-oxo-8,9-anhydroerythromycin A (Compound 1) (see Japanese Patent Application Disclosure HEI No. 6-56873) represented by the following formula:

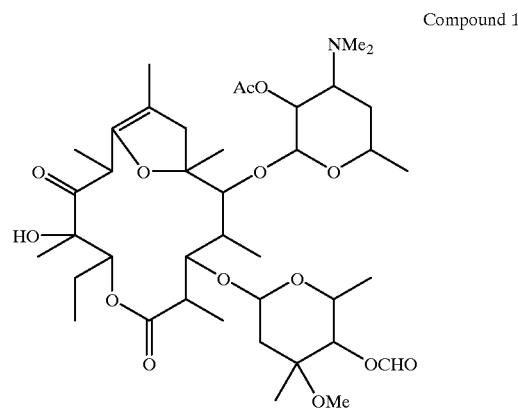

Compound 1 and further 5 ml of 12N—NaOH aqueous solution was added thereto, and the mixture was reacted at room temperature for 2 hours.

After completion of the reaction, the resulting reaction product was neutralized with hydrochloric acid, then THF was distilled off and the residue was extracted with 30 ml of ethyl acetate. The organic layer was washed three times with each 10 ml of a saturated saline solution, dried over magnesium sulfate, filtered, and the solvent in the filtrate was distilled off under reduced pressure to obtain 4.8 g (Yield based on Compound 1 is 99%) of 2'-O-acetyl-11-oxo-8,9-anhydroerythromycin A (Compound 2) as a white powder represented by the following formula:

Compound 2

FAB-MS m/z 756 (MH$^+$)

(2) Into a flask with a volume of 50 ml were charged 3 ml of THF and 0.383 g of sodium hydride (60% in oil), and under argon gas atmosphere, 4.8 g of Compound 2 and 0.2 ml of water were added thereto, and then the mixture was reacted at room temperature for one hour.

After completion of the reaction, the reaction mixture was neutralized with 1N—HCl, THF was distilled off under reduced pressure and the residue was extracted with ethyl acetate. The organic layer was washed with a saline solution and dried over anhydrous magnesium sulfate. The solvent was distilled off under reduced pressure, and the resulting residue was purified by silica gel column chromatography (an eluent; chloroform:methanol:conc. aqueous ammonia= 95:5:0.5) to obtain 3 g (Yield based on Compound 2 is 68%) of Compound 3 as a white powder represented by the following formula:

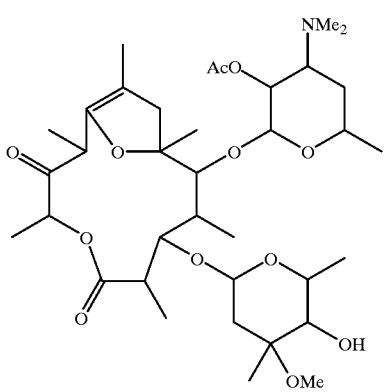

Compound 3

FAB-MS m/z 698(MH$^+$)

Example 2

In 20 ml of methanol was dissolved 3.0 g of Compound 3, and after reacting the mixture at room temperature for 2 days, the mixture was further reacted under heating at 50° C. for 3 hours.

After completion of the reaction, methanol was distilled off from the reaction mixture, and after adding a saturated aqueous sodium hydrogen carbonate solution, the mixture was extracted with ethyl acetate. The organic layer was washed three times with a saturated saline solution, and dried over anhydrous magnesium sulfate, and the solvent was distilled off under reduced pressure. After the resulting residue was dissolved in 3 ml of acetone, 4 ml of a 10% aqueous ammonia was added to the solution and the mixture was stirred at 0° C. for one hour. Precipitated crystals were collected by filtration, and the obtained crystals were dried under reduced pressure at 40° C. for 3 hours to obtain 1.3 g (Yield based on Compound 3 is 46%) of Compound 4 represented by the following formula:

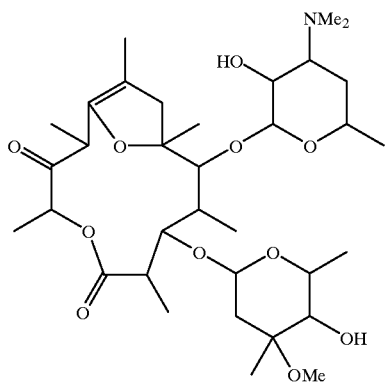

Compound 4

Analytical data of Compound 4 are shown below.
FAB-MS m/z 656 (MH$^+$)
$^1$H-NMR ($\delta$, CDCl$_3$) 5.24 (q, J=6.83 Hz, 1H, H-12), 4.93 (d, J=4.9 Hz, 1H, H-1"), 4.48 (d, J=10.3 Hz, 1H, H-3), 4.36 (d, J=7.3 Hz, 1H, H-1'), 4.05 (dq, J=6.4 Hz, J=9.3 Hz, 1H, H-5"), 3.78 (d, J=9.3 Hz, 1H, H-5), 3.52–3.47 (2H, overlapping, q and m, H-5', H-10), 3.30 (s, 3H, 3"-OMe), 3.20 (dd, J=7.3 Hz, J=9.8 Hz, 1H, H-2'), 3.03 (m, 1H, H-4"), 2.88 (d, q, 1H, H-2), 2.80 (d, J=16.1 Hz, 1H, H-7), 2.50 (ddd, 1H, H-3'), 2.38 (d, J=15.1 Hz, 1H, H-2"), 2.30 (s, 6H, NMe$_2$), 2.03 (d, J=16.1 Hz, 1H, H-7), 1.88 (ddq, J=10.3 Hz, J=8.8 Hz, J=7.3 Hz, 1H, H-4), 1.69 (dddd, 1H, H-4'), 1.58 (dd, J=4.9 Hz, J=15.1 Hz, 1H, H-2"), 1.44 (s, 3H, 8-Me), 1.38–1.31 (9H, overlapping, d, d, and s, 9H, 12-Me, 6-Me, 5"-Me), 1.27–1.14 (16H, overlapping, 2-Me, 5'-Me, 3"-Me, 10-Me, 4-Me, H-4').
$[\alpha]_D^{25}$: −115.70 (c=1.0, CHCl$_3$)

Example 3

Into a four-necked flask with a volume of 200 ml was charged 0.77 g (60% in oil) of sodium hydride, and 30 ml of THF containing 0.34 g of water was added dropwise to the mixture under ice-cooling. After completion of the dropwise addition, the temperature of the mixture was elevated to room temperature, and 10.0 g of Compound 1 dissolved in 10 ml of THF was added dropwise to the mixture. After stirring the mixture at room temperature for 5 hours, 0.78 g (60% in oil) of sodium hydride and 0.33 ml of water was added dropwise with three times by dividing the mixture into three portions. After stirring the mixture at room temperature for 12 hours, 40 ml of methanol and 20 ml of a saturated aqueous sodium hydrogen carbonate solution were added thereto, and the resulting mixture was reacted under heating at 60° C. for 3 hours.

After completion of the reaction, methanol was distilled off from the resulting reaction mixture under reduced pressure, and the residue was extracted with 100 ml of ethyl acetate. The organic layer was washed three times with each 50 ml of a saturated aqueous sodium hydrogen carbonate solution, and the organic layer was dried over anhydrous magnesium sulfate. The solvent was distilled off under reduced pressure, and after 7 ml of acetone and 45 ml of a 10% aqueous ammonia were added to the residue to crystallize the product, the mixture was stirred at 0° C. for one hour. The precipitated crystals were collected by filtration, dried at 50° C. under reduced pressure to obtain 1.02 g of Compound 4 as white crystals.

Example 4

(1) Into a flask with a volume of ml were charged 1.1 g of Compound 4, 10 ml of toluene and 1.73 g of sodium hydrogen carbonate, and the mixture was stirred at room temperature.

Then, 0.5 g of benzyloxycarbonyl chloride was added dropwise thereinto, and after reacting the mixture at room temperature for 2 hours, 2.4 g of benzyloxycarbonyl chloride was further added thereto and the mixture was reacted at 45° C. for 3 hours.

After completion of the reaction, the resulting reaction mixture was cooled to 0° C., and 0.11 g of pyridine dissolved in 2 ml of toluene was added dropwise thereto and the mixture was stirred at 5 to 15° C. for one hour. Further, 8 ml of water was added thereto, the mixture was stirred at room temperature for 10 minutes and extracted with 25 ml of ethyl acetate. The organic layer was washed twice with a saturated saline solution and dried over magnesium sulfate. The solvent was distilled off under reduced pressure to obtain 7.1 g of Compound 5 as viscous oily state represented by the following formula:

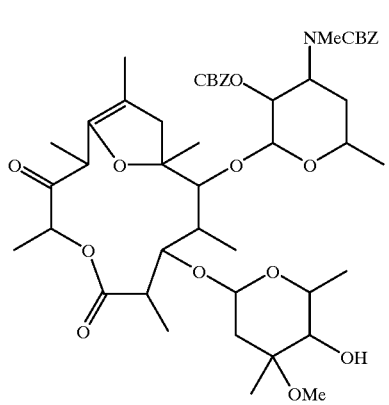

Compound 5

FAB-MS m/z 910 (MH⁺), 412

(2) Into a glass autoclave with a volume of 500 ml were charged 7.1 g of Compound 5, 1.3 g of sodium hydrogen carbonate, 3.3 g of a 10% Pd/C and 50 ml of methanol, and the mixture was reacted under a hydrogen pressure of 3 kg/cm$^2$ at 20 to 30° C. for 6 hours.

After completion of the reaction, the palladium carbon was removed by filtration from the reaction mixture, and the solvent was distilled off under reduced pressure, and the residue was extracted with 80 ml of ethyl acetate. After washing the organic layer with 35 ml of a saturated aqueous sodium hydrogen carbonate solution and further washing with a saturated saline solution twice, the mixture was dried over anhydrous sodium sulfate and the solvent was distilled off under reduced pressure to obtain 0.7 g of a white powder. The resulting powder was recrystallized from 100 ml of acetonitrile to obtain 0.5 g (Yield based on Compound (4) of 46%) of Compound 6 as a white powder represented by the following formula:

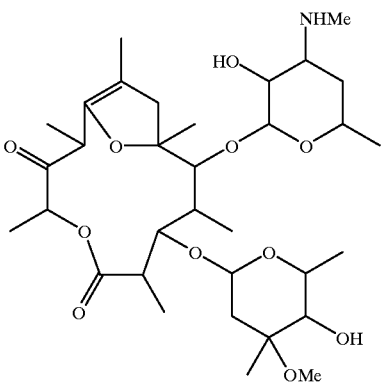

Compound 6

Analytical results of Compound 6 are as shown below.

FAB-MS m/z 642 (MH⁺)

$^1$H-NMR (400 MHz, CDCl$_3$)δ5.23 (q, J=6.83 Hz, 1H, H-12), 4.93 (d, J=4.9 Hz, H-1"), 4.45 (d, J=10.3 Hz, 1H, H-3), 4.35 (d, J=7.8 Hz, 1H, H-1'), 4.04 (dq, 1H, H-5"), 3.79 (d, J=8.8 Hz, 1H, H-5), 3.54 (m, 1H, H-5'), 3.47 (q, J=6.8 Hz, 1H, H-10), 3.30 (s, 3H, 3"-OMe), 3.13 (dd, J=7.4 Hz, J=9.8 Hz, 1H, H-2'), 3.03 (m, 1H, H-4"), 2.86 (dq, 1H, H-2), 2.73 (d, J=16.1 Hz, 1H, H-7), 2.50 (ddd, J=9.7 Hz, J=4.4 Hz, 1H, H-3'), 2.41 (s, 3H, NMe), 2.37 (d, J=15.1 Hz, 1H, H-2"), 2.02 (d, J=16.1 Hz, 1H, H-7), 1.95 (dddd, 1H, H-4'), 1.88 (J=10.3 Hz, J=8.8 Hz, J=7.3 Hz, 1H, H-4), 1.58 (dd, J=4.9 Hz, J=15.1 Hz, 1H, H-2"), 1.44 (s, 3H, 8-Me), 1.36–1.34 (9H, overlapping, d, d, ands, 9H, 12-Me, 6-Me, 5 "-Me), 1.26–1.20 (9H, overlapping, 2-Me, 5'-Me, 3"-Me), 1.20 (d, J=6.83 Hz, 3H, 10-Me), 1.19–1.07 (4H, overlapping, q and ddd, 4-Me, H-4').

$[\alpha]_D^{25}$: −144.20 (c=1.0, CHCl$_3$)

Test Example

Motilin receptor binding test was carried out by the method shown below (see V. Bormans, et al., Regul, Peptides, 15, 143 (1986)). From a slaughtered rabbit was removed the duodenum, of which the mucous membrane was detached from the tunica muscularis and then homogenized in a 50 mM Tris solution (pH 7.4) to prepare a protein solution. After incubating 25 pM $^{125}$I-labeled motilin (available from Otsuka Assay Laboratory) and the protein solution at 25° C. for 120 minutes, radioactivity in the protein solution was measured with a γ-ray counter. The difference between the radioactivity observed in the case of non-addition of motilin and that observed in the case of addition of an excess (1×10$^{-7}$ M) of motilin was defined as the specific binding capacity. The efficacy of the sample was expressed as IC$_{50}$, the concentration of the test drug which reduces the specific binding capacity to 50%. The test drug was dissolved in a DMSO solution and added to the protein solution (the final DMSO concentration: 1%).

As the result, $IC_{50}$ in the dmso solution of compound 4 was $5.7 \times 10^{-9}$ M.

What is claimed is:

1. A compound represented by the formula (I)

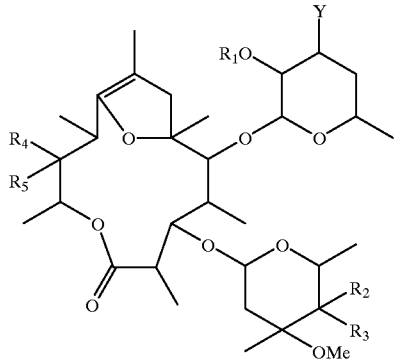

(I)

wherein $R_1$ represents a hydrogen atom or an acyl group; $R_2$ and $R_3$ may be the same or different, and each represents a hydrogen atom, a hydroxyl group, an acyloxy group or an amino group, or $R_2$ and $R_3$ in combination represent =O or =$NOR_{11}$; where $R_{11}$ represents a hydrogen atom or a lower alkyl group; $R_4$ and $R_5$ may be the same or different, and each represents a hydrogen atom or a hydroxyl group, or $R_4$ and $R_5$ in combination represent =O or =$NOR_{11}$; Y represents —$N(R_6)$ $(R_7)$ or —$N^+(R_8)$ $(R_9)$ $(R_{10})X^-$; where $R_6$, $R_7$, $R_8$, $R_9$ and $R_{10}$ may be the same or different, and each represents a hydrogen atom, an acyl group, an unsubstituted or substituted lower alkyl group, an unsubstituted or substituted lower alkenyl group, an unsubstituted or substituted lower alkynyl group, an unsubstituted or substituted cycloalkyl group, or amonocyclic, saturated, 3- to 7-membered heterocyclic ring comprising an oxygen atom, a sulfur atom or a nitrogen atom as a hetero atom which may have a substituent(s), or $R_6$ and $R_7$, or $R_8$ and $R_9$ may form an azacycloalkyl group together with the neighboring nitrogen atom, respectively; and $X^-$ represents an anion,
or a salt thereof.

2. The compound or a salt thereof according to claim 1, wherein $R_1$ and $R_2$ are hydrogen atoms, $R_3$ is a hydrogen atom, a hydroxyl group or an amino group, or $R_2$ and $R_3$ in combination represent =O or =N—$OR_{11}$; where $R_{11}$ is a hydrogen atom or a lower alkyl group, $R_4$ and $R_5$ in combination represent =O, Y represents —$N(R_6)$ $(R_7)$ or —$N^+(R_8)$ $(R_9)$ $(R_{10})X^-$; where $R_6$, $R_7$, $R_8$, $R_9$ and $R_{10}$ may be the same or different, and each represents a hydrogen atom, an unsubstituted or substituted lower alkyl group, an unsubstituted or substituted lower alkynyl group, an unsubstituted or substituted lower alkenyl group, an unsubstituted or substituted cycloalkyl group, or amonocyclic, saturated, 3- to 7-membered heterocyclic ring comprising an oxygen atom, a sulfur atom or a nitrogen atom as a hetero atom which may have a substituent(s), and the substituent is a hydroxyl group(s), an amino group(s), a halogen atom(s), a cyano group(s), an alkyloxy group(s), a mercapto group(s), an acyl group(s) or a carbamoyl group(s), and $X^-$ represents an anion.

3. A pharmaceutical composition which comprises the compound(s) according to claim 2 or salt(s) thereof.

4. A pharmaceutical composition according to claim 3, wherein it is a stimulant for the contractile motility of alimentary canals.

5. A process for producing the compound according to claim 1 or a salt thereof, which comprises reacting a compound represented by the formula (II):

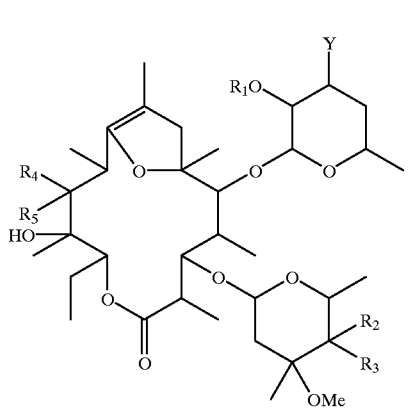

(II)

wherein $R_1$, $R_2$, $R_3$, $R_4$, $R_5$ and Y have the same meanings as defined in claim 1, with a base to convert the compound to a 13-membered macrolide compound.

6. A method of stimulating contractile mobility of alimentary canals in a warm-blooded animal comprising administering to a warm-blooded animal an effective amount of a compound of claim 2 sufficient to stimulate contractile mobility of alimentary canals.

* * * * *